United States Patent
McCarthy

(10) Patent No.: US 9,562,040 B2
(45) Date of Patent: Feb. 7, 2017

(54) PROCESSES FOR PREPARING RIVAROXABAN

(71) Applicant: INDIANA UNIVERSITY RESEARCH AND TECHNOLOGY CORPORATION, Indianapolis, IN (US)

(72) Inventor: James R. McCarthy, Indianapolis, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 81 days.

(21) Appl. No.: 14/390,527

(22) PCT Filed: Apr. 4, 2013

(86) PCT No.: PCT/US2013/035235
§ 371 (c)(1),
(2) Date: Oct. 3, 2014

(87) PCT Pub. No.: WO2013/152168
PCT Pub. Date: Oct. 10, 2013

(65) Prior Publication Data
US 2015/0175590 A1    Jun. 25, 2015

Related U.S. Application Data

(60) Provisional application No. 61/621,208, filed on Apr. 6, 2012.

(51) Int. Cl.
| | | |
|---|---|---|
| C07D 413/14 | (2006.01) |
| C07D 413/10 | (2006.01) |
| C07D 303/36 | (2006.01) |
| C07D 301/02 | (2006.01) |

(52) U.S. Cl.
CPC ........... *C07D 413/14* (2013.01); *C07D 301/02* (2013.01); *C07D 303/36* (2013.01); *C07D 413/10* (2013.01)

(58) Field of Classification Search
CPC .................................................. C07D 413/14
See application file for complete search history.

(56) References Cited

U.S. PATENT DOCUMENTS

| | | | |
|---|---|---|---|
| 7,816,355 B1* | 10/2010 | Bodhuri | A61K 31/5377 |
| | | | 514/236.8 |
| 9,206,141 B2 | 12/2015 | McCarthy | |
| 2002/0086900 A1 | 7/2002 | Perrault et al. | |

FOREIGN PATENT DOCUMENTS

| | | | |
|---|---|---|---|
| CN | 101638392 A | | 2/2010 |
| CN | 102250076 A | | 11/2011 |
| EP | 2404920 A1 | * | 1/2012 |
| WO | WO-2011/098501 A1 | * | 8/2011 |
| WO | 2011/137222 A1 | | 11/2011 |
| WO | WO-2012/032533 A2 | * | 3/2012 |
| WO | 2012/153155 A1 | | 11/2012 |
| WO | 2012/159992 A1 | | 11/2012 |
| WO | WO-2013/046211 A1 | * | 4/2013 |

OTHER PUBLICATIONS

Chemical Abstracts Registry No. 1345879-72-2, indexed in the Registry file on STN CAS Online Nov. 18, 2011.*
Li et al., Journal of Chemical Research, Jul. 2011, 35(7), pp. 400-401.*
An English translation of CN 102250076 A, Zhang et al., Nov. 23, 2011.*
PCT International Search Report and Written Opinion completed by the ISA/EP on May 13, 2013 and issued in connection with PCT/US2013/035235, May 17, 2013.
Gregory, W. A. et al., "Antibacterials. Synthesis and structure-activity studies of 3-aryl-2-oxooxazolidines. 2. The 'A' group," 1990, J. Med. Chem., 33, 2569-2578.

* cited by examiner

*Primary Examiner* — Laura L. Stockton
(74) *Attorney, Agent, or Firm* — Barnes & Thornburg LLP

(57) ABSTRACT

Processes and intermediates for preparing rivaroxaban, and analogs and derivatives thereof, and pharmaceutically acceptable salts of each of the foregoing, are described herein.

18 Claims, No Drawings

PROCESSES FOR PREPARING RIVAROXABAN

CROSS REFERENCE TO RELATED APPLICATIONS

This application is a national stage entry under 35 USC §371(b) of International Application No. PCT/US2013/035235, filed Apr. 4, 2013, which claims priority under 35 U.S.C. §119(e) to U.S. Provisional Application Ser. No. 61/621,208, filed Apr. 6, 2012, the disclosure of which is incorporated herein in its entirety.

TECHNICAL FIELD

The invention described herein pertains to processes for preparing rivaroxaban, and analogs and derivatives thereof, and pharmaceutically acceptable salts of each of the foregoing.

BACKGROUND AND SUMMARY OF THE INVENTION

Rivaroxaban is an oral anticoagulant. Rivaroxaban is a direct factor Xa inhibitor. It has been reported that rivaroxaban may replace warfarin in the treatment and prevention of strokes and heart attacks, with a market potential well over a billion USD per year. Accordingly, efficient, economical, and high yielding processes for preparing rivaroxaban are needed.

It has been discovered herein that rivaroxaban may be prepared directly via a 1,3-cycloaddition reaction, as described herein. However, the starting materials needed for such a process have been observed herein to be highly insoluble. Surprisingly, the quite insoluble starting materials are converted to intermediates under the solution-based reaction conditions described herein. Moreover, it has also been discovered herein that intermediates in the process for preparing rivaroxaban crystallize from the reaction mixture in highly purified form.

Described herein are efficient processes for the preparation of rivaroxaban and pharmaceutically acceptable salts thereof. In one embodiment, the processes described herein include the step of preparing the oxazolidinone present in rivaroxaban and pharmaceutically acceptable salts thereof from an oxirane and an isocyanate.

In one illustrative embodiment of the inventions described herein, the processes include the step of preparing 4-(4-morpholin-2-onyl)phenyl isocyanate from 4-(4-morpholin-2-onyl)aniline, or a salt thereof, and an acylating agent. In another embodiment, the processes include the step of preparing a compound of the formula

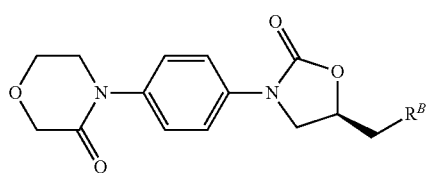

or a salt thereof from 4-(4-morpholin-2-onyl)phenyl isocyanate and an oxirane of the formula

where $R^A$ is halo or a protected amino group; and $R^B$ is halo, amino, or a protected amino group.

In another embodiment, the processes include the step of preparing a compound of the formula

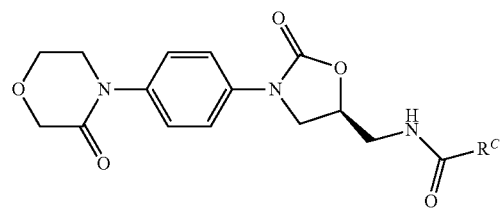

or a salt thereof from

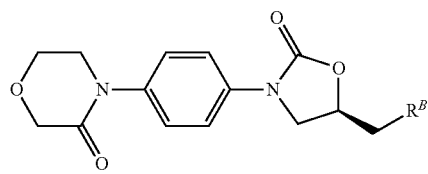

or a salt thereof, and an acylating agent.

In another embodiment, the processes include the step of preparing a compound of the formula

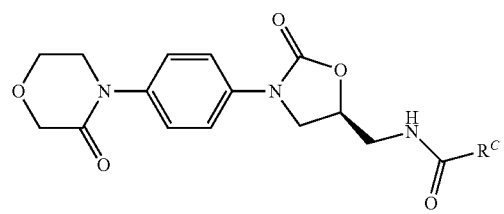

or a salt thereof from

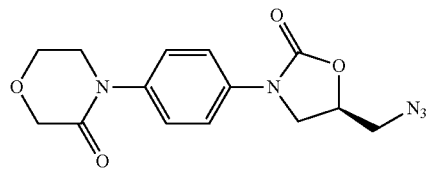 [SMILES: [N-]=[N+]=NC[C@H]1CN(c2ccc(N3CCOCC3=O)cc2)C(=O)O1]

or a salt thereof, and $R^C C(O)SH$, where $R^C$ is alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted.

In another embodiment, described herein are process that proceed in high overall yield. In another embodiment, described herein are process that require minimal purifications using chromatography, or alternatively, do not require any purifications using chromatography. In another embodiment, described herein are process where the products from each step are isolated as solids and/or crystalline solids. In another embodiment, described herein are process that proceed with high enantiomeric excess. It is to be understood that the processes described herein may be performed using racemic material and to produce racemic material, or using optically active material to produce optically active material of either absolute configuration. It is also to be understood that the processes described herein may be routinely adapted to prepare any of a wide variety of materials having a predetermined enanatiomeric excess or a predetermined range of enanatiomeric excess.

DETAILED DESCRIPTION

In one illustrative embodiment, described herein is a process for preparing rivaroxaban or a pharmaceutically acceptable salt thereof. Further illustrative embodiments are described in the following numbered clauses:

1. A process for preparing rivaroxaban or a pharmaceutically acceptable salt thereof, the process comprising one or steps selected from the group consisting of
(a) mixing a compound of formula (A)

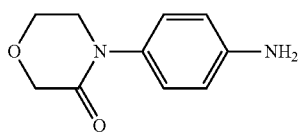

(A)

or a salt thereof, with an acylating agent to prepare a compound of formula (B)

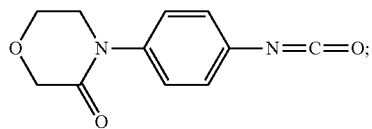

(B)

(b) crystallizing the compound of formula (B);
(c) mixing the compound of formula (B) with a compound of formula (C)

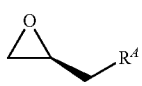

(C)

to prepare a compound of formula (D)

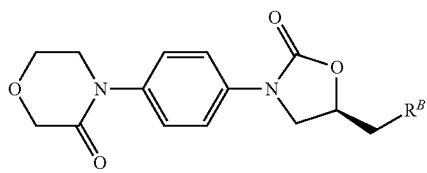

(D)

or a salt thereof; where $R^A$ is halo or a protected amino group; and $R^B$ is halo, amino or a salt thereof, or a protected amino group;

(d) crystallizing the compound of formula (D);
(e) converting the compound of formula (D) or a salt thereof, where $R^B$ is halo, or a protected amino group, into a compound of formula (E)

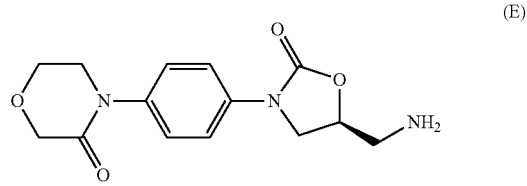 [SMILES: NC[C@H]1CN(c2ccc(N3CCOCC3=O)cc2)C(=O)O1]

(E)

or a salt thereof;
(f) converting the compound of formula (D) or a salt thereof, where $R^B$ is halo, or a protected amino group, into a compound of formula (F)

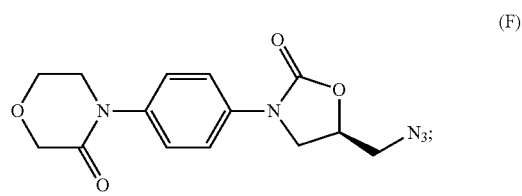 [SMILES: [N-]=[N+]=NC[C@H]1CN(c2ccc(N3CCOCC3=O)cc2)C(=O)O1]

(F)

(g) reducing the compound of formula (F) or a salt thereof, into a compound of formula (E)
(h) mixing the compound of formula (E) or a salt thereof with an acylating agent to prepare rivaroxaban, or a salt thereof; and
(i) crystallizing rivaroxaban or a salt thereof from an organic acid; and combinations thereof.

2. The process of clause 1 wherein the organic acid is an alkyl carboxylic acid.
3. The process of clause 1 wherein the organic acid is acetic acid.
4. The process of clause 1 wherein the organic acid is propionic acid or propanoic acid.
5. The process of any one of clauses 1 to 4 wherein the acylating agent in step (a) is phosgene or a phosgene analog.
6. The process of any one of clauses 1 to 5 comprising step (b).
7. The process of any one of clauses 1 to 6 comprising step (c).
8. The process of any one of clauses 1 to 7 wherein the compound of formula (C) is a compound of the formula

9. The process of any one of clauses 1 to 7 wherein the compound of formula (C) is a compound of the formula

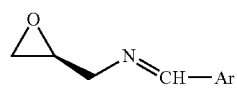

where Ar is optionally substituted phenyl.
10. The process of clause 9 wherein Ar is phenyl.

11. The process of clause 9 wherein Ar is 4-chlorophenyl.

12. The process of any one of clauses 1 to 11 wherein $R^B$ is an imine.

13. The process of any one of clauses 1 to 11 wherein $R^B$ is optionally substituted benzylidene amino.

14. The process of any one of clauses 1 to 11 wherein $R^B$ is benzylidene amino, 4-chlorobenzylidene amino; 4-bromobenzylidene amino; or 2,4-dichlorobenzylidene amino.

15. The process of any one of clauses 1 to 11 wherein $R^B$ is benzylidene amino.

16. The process of any one of clauses 1 to 15 wherein the reducing agent is hydrogen gas.

17. The process of any one of clauses 1 to 16 wherein step (g) includes a metal or metal catalyst.

18. The process of any one of clauses 1 to 17 wherein step (c) includes a halide catalyst.

19. The process of clause 18 wherein the halide catalyst is $Br^-$.

20. The process of clause 18 wherein the halide catalyst is magnesium bromide etherate, lithium bromide, or lithium bromide in combination with a phosphine oxide, such as tri-n-butylphosphine oxide.

21. A process for preparing a compound of the formula

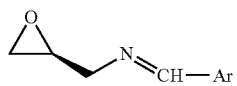

where Ar is optionally substituted phenyl;
the process comprising the step of mixing a compound of the formula

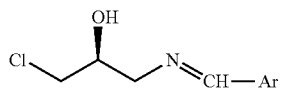

with a base.

22. A compound of the formula

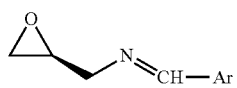

where Ar is optionally substituted phenyl.

23. The process of clause 21 or compound of clause 22 wherein Ar is phenyl.

24. The process of clause 21 or compound of clause 22 wherein Ar is 4-chlorophenyl.

It is to be understood that in the foregoing embodiments, processes are described that include one or more of any of the steps, two or more of any of the steps, three or more of any of the steps, and so on. For example, processes are described herein that include step (b); processes are also described herein that include steps (b) and (c); processes are also described herein that include steps (b) and (d); processes are also described herein that include steps (b), (c), and (d); and so on.

It is also to be understood that in step (c) the $R^A$ group on the oxirane and the $R^B$ group on the oxazolidinone can be the same. Illustratively, when $R^A$ is halo, such as chloro, $R^B$ is halo, such as chloro; and when $R^A$ is a protected amino group, $R^B$ is a protected amino group. However, it is also to be understood that $R^A$ may be converted to a different $R^B$ in step (c) and still fall within the scope of the process step. For example, when $R^A$ is halo, such as chloro, $R^B$ may be amino or a protected amino if other components are added to the mixture that are capable of concomitantly or sequentially converting the halo, such as chloro, to amino or a protected amino. Similarly, when $R^A$ is a protected amino, $R^B$ may be amino if other components are added to the mixture that are capable of concomitantly or sequentially converting the protected amino to amino.

In another embodiment, described herein is the process as in any of the preceding embodiments wherein the reducing agent is hydrogen gas.

In another embodiment, described herein is the process as in any of the preceding embodiments wherein the acylating agent is phosgene or a phosgene analog. Illustrative phosgene analogs include diphosphogene, triphosgene, carbonyldiimidazole, and the like.

In another embodiment, described herein is the process as in any of the preceding embodiments, comprising step (b).

In another embodiment, described herein is the process as in any of the preceding embodiments wherein the oxirane is a compound of the formula

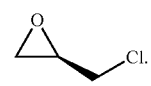

In another embodiment, described herein is the process as in any of the preceding embodiments wherein the oxirane is a compound of the formula

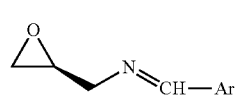

where Ar is optionally substituted phenyl.

In another embodiment, described herein is the process as in any of the preceding embodiments wherein Ar is phenyl.

In another embodiment, described herein is the process as in any of the preceding embodiments wherein Ar is 4-chlorophenyl.

In another embodiment, described herein is the process as in any of the preceding embodiments wherein $R^A$ is an imine.

In another embodiment, described herein is the process as in any of the preceding embodiments wherein $R^A$ is benzylidene amino, where the benzyl is optionally substituted.

In another embodiment, described herein is the process as in any of the preceding embodiments wherein $R^A$ is benzylidene amino, 4-chlorobenzylidene amino; 4-bromobenzylidene amino; or 2,4-dichlorobenzylidene amino.

In another embodiment, described herein is the process as in any of the preceding embodiments wherein $R^A$ is benzylidene amino.

In another embodiment, described herein is the process as in any of the preceding embodiments wherein $R^B$ is an imine.

In another embodiment, described herein is the process as in any of the preceding embodiments wherein $R^B$ is benzylidene amino, where the benzyl is optionally substituted.

In another embodiment, described herein is the process as in any of the preceding embodiments wherein $R^B$ is benzylidene amino, 4-chlorobenzylidene amino; 4-bromobenzylidene amino; or 2,4-dichlorobenzylidene amino.

In another embodiment, described herein is the process as in any of the preceding embodiments wherein $R^B$ is benzylidene amino.

In another embodiment, described herein is a process for preparing a compound of the formula

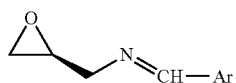

where Ar is optionally substituted phenyl;

the process comprising the step of mixing a compound of the formula

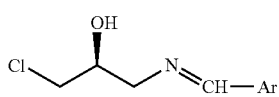

with a base.

In another embodiment, described herein is a compound of the formula

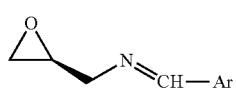

where Ar is optionally substituted phenyl.

In another embodiment, described herein is the process or compound of any of the preceding embodiments wherein Ar is phenyl.

In another embodiment, described herein is the process or compound of any of the preceding embodiments wherein Ar is 4-chlorophenyl.

In another embodiment, described herein is a process for preparing 3-fluoro-4-(1-morpholino)phenyl isocyanate, where the process includes the step of mixing 3-fluoro-4-(1-morpholino)aniline, or a salt thereof, with an acylating agent.

In another embodiment, described herein is the process as in any of the preceding embodiments wherein the acylating agent is phosgene or a phosgene analog.

In another embodiment, described herein is a compound of formula (B)

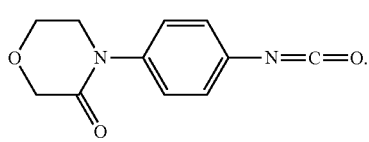

In another embodiment, described herein is a compound of formula (D)

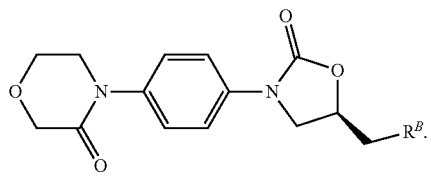

or a salt thereof; where $R^A$ is halo or a protected amino group; and $R^B$ is halo, amino, or a protected amino group;

In another embodiment, described herein is a compound of formula (F)

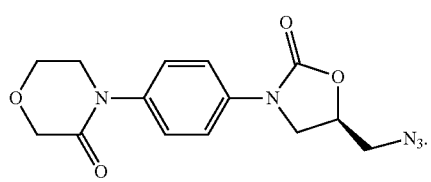

In another embodiment, described herein is a process for preparing rivaoxaban using the following steps:

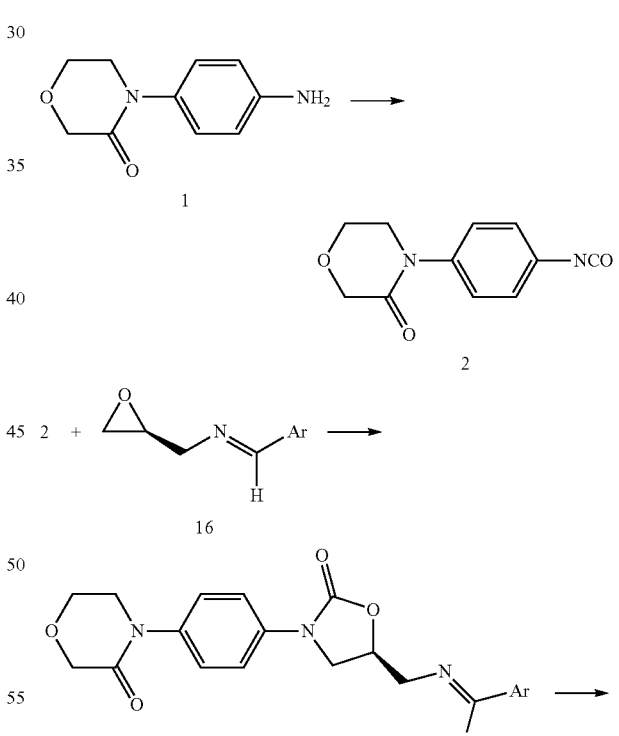

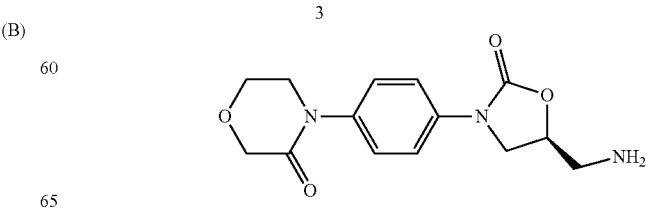

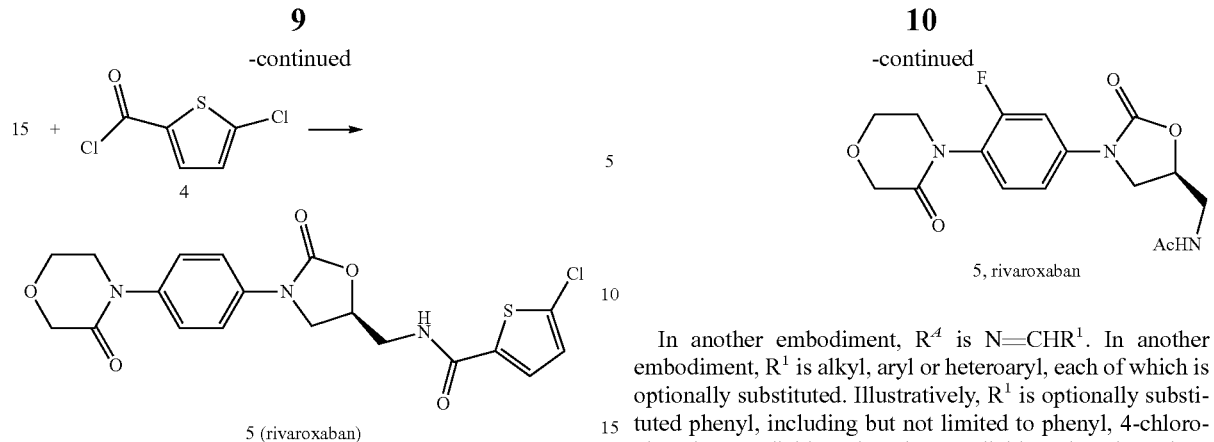

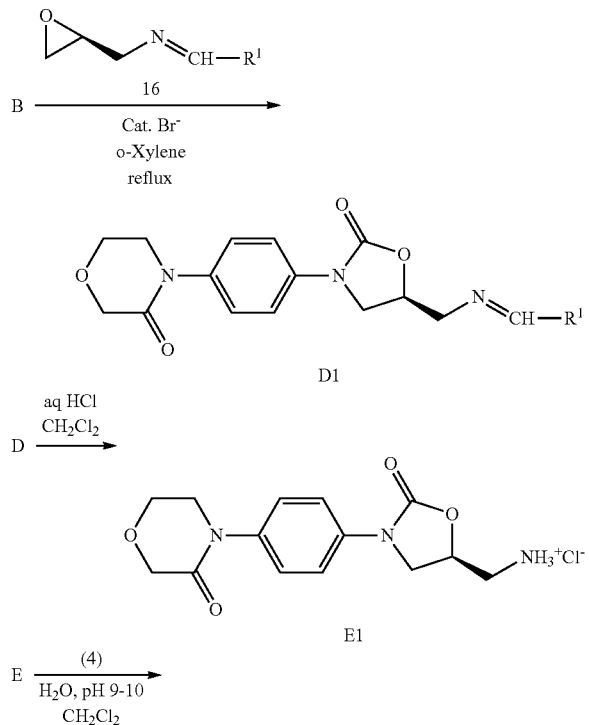

where Ar is optionally substituted aryl or heteroaryl, including optionally substituted phenyl.

In another embodiment, described herein is a convergent process for the preparation of the antibiotic rivaroxaban starting from a compound of formula (A). In one aspect, the convergent process provides rivaroxaban in an overall yield of 71%. In another embodiment, processes described herein are used to prepare rivaroxaban having an enantiomeric excess of about 97% or greater, about 98% or greater, or about 99% or greater. In another aspect, the processes described herein avoid the use of expensive reagents such as lithium t-butoxide and (R)-glycidyl butyrate.

In another embodiment, catalytic sources of Br⁻ are included in the processes described herein for preparing compounds of formula (D). Illustrative catalytic sources of Br⁻ include, but are not limited to, magnesium bromide etherate, lithium bromide in combination with a phosphine oxide, such as tri-n-butylphosphine oxide, and the like.

In another embodiment, $R^A$ is N=CHR$^1$. In another embodiment, $R^1$ is alkyl, aryl or heteroaryl, each of which is optionally substituted. Illustratively, $R^1$ is optionally substituted phenyl, including but not limited to phenyl, 4-chlorophenyl, 2,4-dichlorophenyl, 2,6-dichlorophenyl, 4-bromophenyl, 4-nitrophenyl, and the like. Illustratively, $R^1$ is phenyl.

In another embodiment, analogs and derivatives of rivaroxaban are described herein. Illustrative analogs and derivatives of rivaroxaban include compounds of formula (G)

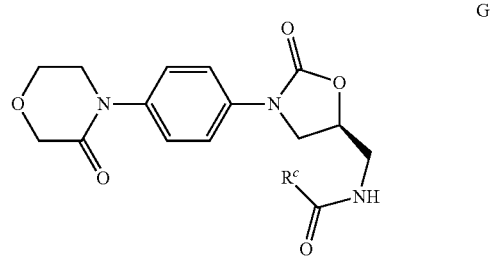

and salts thereof. In another embodiment, processes for preparing analogs and derivatives of rivaroxaban are described herein. Illustrative processes for preparing analogs and derivatives of rivaroxaban include processes for preparing compounds of formula (G) from compounds of formula (E) and an acylating agent, such as an acylating agent of formula $R^C$—C(O)-L, where $R^C$ is as defined herein in the various embodiments, and L is a leaving group or activating group. Illustrative processes include the following

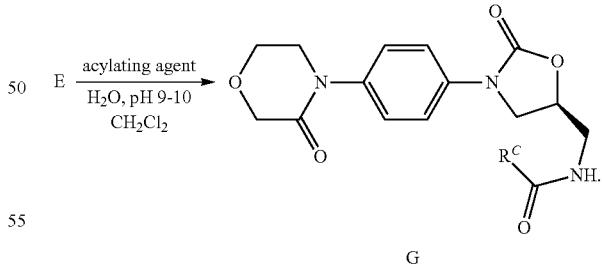

In another embodiment, compounds (B), such as compound (2), in the above scheme precipitates or crystallizes from the reaction mixture, and may be optionally further purified by crystallization. It has been unexpectedly discovered that compounds (B), such as compound (2), when $R^1$ is unsubstituted phenyl, is also isolable from the reaction mixture as a solid or crystalline solid. It is also surprisingly observed that compounds (B) are quite insoluble in organic solvents, in particular, non-polar organic solvents. It is also surprisingly observed that compounds (B), though quite insoluble in organic solvents, in particular, non-polar organic solvents, nevertheless react to form compounds (D). It is also surprisingly observed that compounds (B), though quite insoluble in aromatic solvents, such as benzene, toluene, xylenes, and the like, nevertheless react to form compounds (D).

In another embodiment, compounds (D), such as compound (3), in the above scheme precipitates or crystallizes from the reaction mixture, and may be optionally further purified by crystallization. It is surprising observed that compounds (D) may be recrystallized from alcohols, such as ethanol.

It is also surprisingly observed that rivaroxaban precipitates or crystallizes from the reaction mixture. Though without being bound by theory, it is believed herein that the possibility of purifying intermediate compounds, such as compounds of formula (D), by recrystallization provides rivaroxaban in substantially higher purity. Rivaroxaban may accordingly be used without further purification. Recrystallization of rivaroxaban is observed to be quite difficult. For example, recrystallization of rivaroxaban from alcohols, such as methanol requires a substantial excess of solvent. Without being bound by theory, such a substantial excess of solvent is believed to be economically precluded. It is surprisingly observed that rivaroxaban recrystallizes from organic acids. In one variation, rivaroxaban is recrystallized from an organic acid, including alkyl carboxylic acids such as acetic acid, propionic acid, also referred to as propanoic acid, and the like.

In another embodiment, described herein is a process for the conversion of isocyanates, such as compound (2) into rivaroxaban using epichlorohydrins. In another illustrative embodiment, the processes include the following sequence of steps:

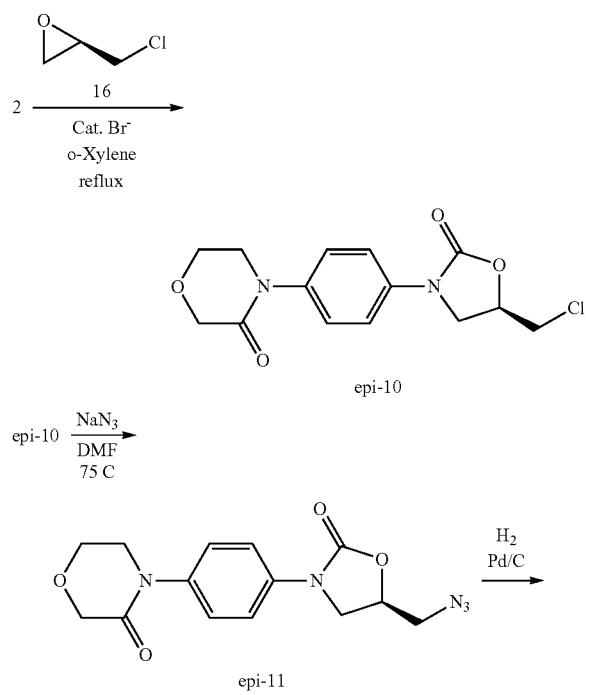

-continued

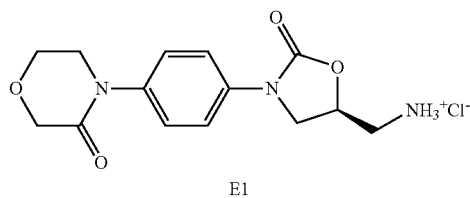

E1

In another embodiment, described herein is a process for the conversion of azides, such as compounds (11) into rivaroxaban or analogs thereof in one step:

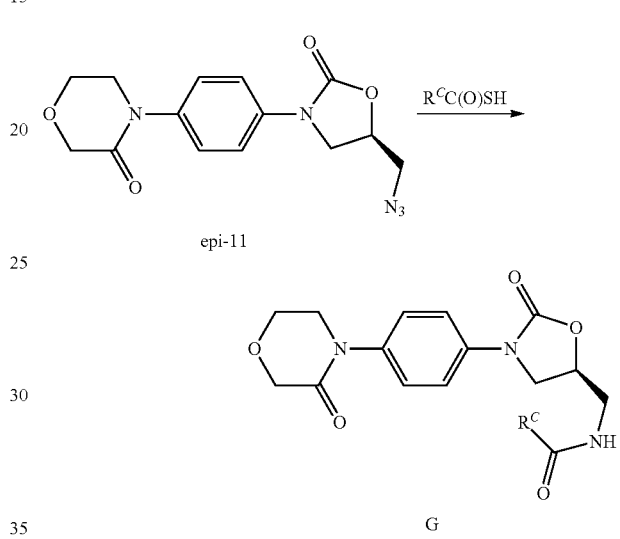

In another illustrative embodiment, imine or Schiff base epoxide intermediates such as those illustrated herein for compound (C1), and processes for preparing them are described. Illustratively, compounds (C1) may be prepared as illustrated in the following scheme

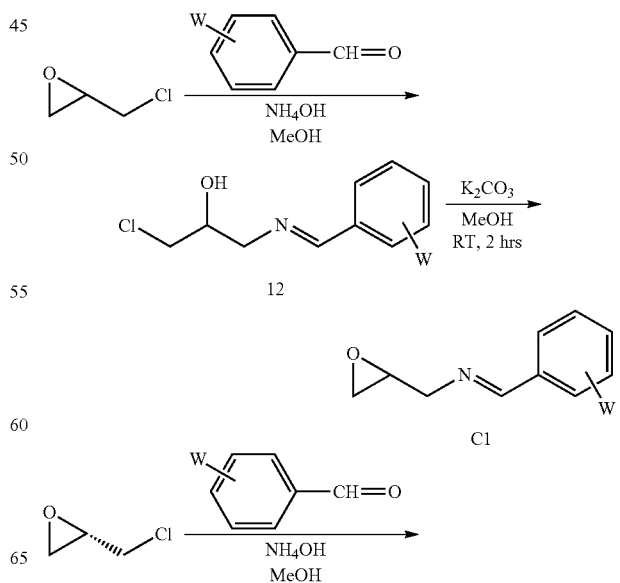

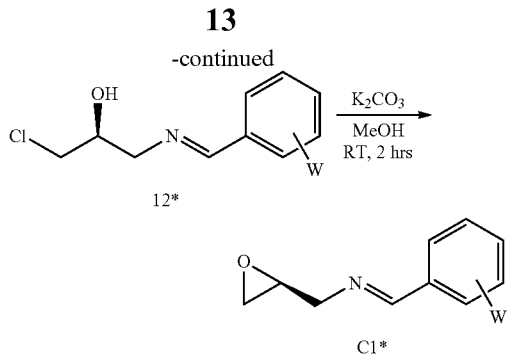

where $R^4$ is N=$CHR^1$, where $R^1$ is W-substituted phenyl. In another embodiment, W represents one or more substituents as described herein. It is to be understood that the imines described herein may be either in a (Z) or (E) configuration, or any of a wide variety of mixtures thereof. Without being bound by theory, it is believed herein that the arylalkylidene imines are typically in, or predominantly in, the (E) configuration, as shown herein for compounds such as (12) and (C1). Illustratively, when W is 4-chloro, the preparation of (12) and (12*) proceeds in about 75% yield from epichlorohydrin, and that of (C1) and (C1*) in about quantitative yield.

The preparation of rivaroxaban has been proposed or disclosed in other publications, such as WO 2001/047919, IL 176767, US 2007/0149522, US 2010/0081807, U.S. Pat. No. 7,816,355, EP 2354128 (WO 2011/09850), US 2011/0034465, and WO 2011/080341.

EXAMPLES

The following examples further illustrate specific embodiments of the invention. However, the following examples should not be interpreted in any way to limit the invention. Characterization of compounds described herein may be performed using MS chromatography, such as LCMS according to the following conditions:

Column and solvents: Agilent Eclipse XDB-C18, 5 uM, 150×4.6 mm; Solvent A: 5 mM Ammonium acetate in Water; Solvent B: 5 mM Ammonium acetate in $CH_3CN$:MeOH (1:1); Method: Time 0 min 50% B, Time 20 min 100% B, Stop Time 20.0 min, Gradient elution flow rate 1.00 mL/min Column and solvents: Inertsil Ph, 5 micron, 250×4.6 mm; Solvent A: 1.36 g $KH_2PO_4$ in 1000 mL $H_2O$, adjust to pH 7.0 with 1N KOH; Solvent B: $CH_3CN$; Method: Time 0 min 70% B, Time 8 min 70% B, Time 15 min 50% B, Time 30 min 30% B, Time 40 min 30% B, Stop time: 40 min, Gradient elution flow rate 1.00 mL/min Column and solvents: Chiralcel OJ (Lot No. 168-053-40615) (Daicel Chemical Indust.) 250×4.6 mm Cellulose-tris(4-methylbemzoate) coated with 10 um silica gel; Method: Time 0 min: 20% B, Time 60 min 100% B, Gradient elution flow rate 1.00 ml/min; It is to be understood that these conditions may be used for chiral chromatography LCMS analysis of the enantiomeric excess (ee), such as for compound (5).

Example 4-(3-Oxomorpholino)phenyl isocyanate (2)

Triphosgene (1 gm, 3.37 mmol) and 4-(4-aminophenyl)morpholin-3-one[1] (1) (1 gm, 5.2 mmol) were added to a 250 ml round bottom flask under argon with football stirrer and reflux condenser that has a gas inlet value on top. Dry toluene (100 ml) was added and the reaction was heated at reflux for 4 hours with stirring. The reaction mixture was cooled to ambient temperature and filtered from the dark insoluble material and washed with toluene (5 ml). The colorless filtrate was cooled to −15° C. overnight and the resulting white crystals (750 mg, 57%) were collected by filtration, washed with hexane and dried in a vacuum oven at 30° C. IR (thin film) 2270 cm-1. NMR (CDCl3, 500 MHz) δ 7.23 (d, J=8.7 Hz, 2H), 7.07 (d, J=8.7 Hz, 2H), 4.27 (s, 2H), 3.97 (dd, J=5.2 Hz, J=4.8 Hz, 2H), 3.68 (dd, J=5.2 Hz, J=5.2 Hz, 2H).

Example 4-(3-Oxomorpholino)phenyl isocyanate (2)

Triphosgene (60 g, 312 mmol) and 4-(4-aminophenyl)morpholin-3-one[1] (1) (60 g, 202 mmol) were added to a 3 L-3 neck round bottom flask under argon with overhead stirrer and reflux condenser that has a gas inlet value on top. Dry toluene (2.25 L) was added and the reaction was heated at reflux with stirring. After 6.5 hours the glass stopper was removed from the 3 L flask and the reaction was allowed to concentrate to ca. 1.7 L. The reaction mixture was cooled in the freezer (−15° C.) overnight and the resulting light yellow crystals (44.6 g) were collected by filtration, washed with hexane and dried in a vacuum oven at 30° C. An additional 21 g (total yield 65.6 g, 84%) of off-white crystals of 2 were isolated by evaporating the filtrate to dryness and triturating the crystals with hexane, collecting by filtration and drying in a vacuum oven at 30° C. IR (thin film) 2270 cm-1. NMR (CDCl3, 500 MHz) δ 7.23 (d, J=8.7 Hz, 2H), 7.07 (d, J=8.7 Hz, 2H), 4.27 (s, 2H), 3.97 (dd, J=5.2 Hz, J=4.8 Hz, 2H), 3.68 (dd, J=5.2 Hz, J=5.2 Hz, 2H).

Example (S)-(E,Z)-5-((4-Chlorobenzylideneamino)methyl)-3-(4-morpholin-3-onephenyl)oxazolidin-2-one (3)

Anhydrous LiBr (20 mg, 0.22 mmol) and tri-n-butylphosphine oxide (55 mg, 0.25 mmol) were quickly added to a 50 ml 3-neck round bottom flask containing toluene (5 ml) and a football-stirring bar under an argon atmosphere, rinsing in the reagents with toluene (5 ml). The mixture was refluxed for 30 minutes under argon allowing toluene to distill from the reaction flask, to remove water, resulting in a clear solution. A room temperature slurry of 4-(3-oxomorpholino)phenyl isocyanate (2) (750 mg, 3 mmol) and (S) (E,Z)-N-4-chlorobenzylidene-1-(oxiran-2-yl)methanamine (8) (730 mg, 3.75 mol) in toluene (10 ml) was added to the refluxing reaction over ca. 2 minutes resulting in vigorous bubbling. The essentially homogenous reaction was heated at reflux for one hour, removed from the oil bath and decanted from a small amount of insoluble material adhering to the bottom of the reaction flask into hexane (100 ml) that was rapidly stirring. The resulting white precipitate was collected by filtration, washed with hexane and dried in vacuo at 35° C. (1.0 gm, 80%). A small sample was recrystallized from toluene. $^1$H NMR (500 MHz, DMSO-d6) δ 8.47 (s, 1H), 7.73 (d, 2H, J=8.6 Hz), 7.58 (d, 2H, J=9.0 Hz), 7.51 (d, 2H, J=8.5 Hz), 7.40 (d, 2H, J=9.0 Hz), 5.03 (m 1H), 4.24 (dd, 1H, J=9.0 Hz, J=9.0 Hz), 4.20 (s, 2H), 4.00-3.96 (m 3H), 3.92 (dd, 2H, J=4.6 Hz, J=4.6 Hz), 3.71 (dd, 2H, J=5.2 Hz, J=5.2 Hz).

Example (S)-(E,Z)-5-((4-Chlorobenzylideneamino)methyl)-3-(4-morpholin-3-onephenyl)oxazolidin-2-one (3)

Anhydrous LiBr (1.15 g, 13 mmol) and tri-n-butylphosphine oxide (3.25 g, 15 mmol) were quickly added to a 3 L-3 neck round bottom flask containing toluene (100 ml) under an argon atmosphere with overhead stirrer, and reflux condenser with an argon inlet tube, rinsing in the reagents with toluene (400 ml). The mixture was refluxed for 30 minutes under argon allowing a small amount of toluene to distill from the reaction flask, to remove water, resulting in a clear colorless solution. A room temperature slurry of 4-(3-oxomorpholino)phenyl isocyanate (2) (44.6 g, 178.4 mmol) and (S) (E,Z)-N-4-chlorobenzylidene-1-(oxiran-2-yl)methanamine (8) (35.2 g, 180 mol) in toluene (500 ml) was added to the refluxing reaction mixture portion wise over ca. 10 minutes resulting in vigorous bubbling. The essentially homogenous reaction was heated at reflux for one hour. The golden yellow reaction solution was removed from the heating mantle and filtered through fluted filter paper into a 2 L Erlenmeyer flask to remove a small amount of white insoluble material adhering to the bottom of the reaction flask, rinsing with hot toluene (200 ml). The filtrate was stirred and hexane (500 ml) was added. The resulting off-white precipitate was allowed to stir for 3 hours forming a crystalline light yellow solid. The solid was collected by filtration, washed with hexane and dried in vacuo at 35° C. (75 g, quantitative yield). Recrystallization from absolute ethanol (800 ml) filtering through fluted filter paper (keeping at reflux to avoid premature crystallization) provided a mass of white crystals on cooling to ambient temperature with stirring. The crystalline mixture was cooled in an ice bath and the crystals were collected by filtration, washing with cold (−15° C.) ethanol and then with hexane and dried in a vacuum oven (67 g, 90.7%). $^1$H NMR (500 MHz, DMSO-d6) δ 8.47 (s, 1H), 7.73 (d, 2H, J=8.6 Hz), 7.57 (d, 2H, J=9.0 Hz), 7.50 (d, 2H, J=8.5 Hz), 7.40 (d, 2H, J=9.0 Hz), 5.03 (m 1H), 4.24 (dd, 1H, J=9.0 Hz, J=9.0 Hz), 4.20 (s, 2H), 4.00-3.96 (m 3H), 3.92 (dd, 2H, J=4.6 Hz, J=4.6 Hz), 3.71 (dd, 2H, J=5.2 Hz, J=5.2 Hz).

Example

5-Chloro-2-thiophenecarbonyl chloride (4)

5-Chlorothiophene-2-carboxylic acid (975 mg, 6 mmol) was placed in a 25 ml round bottom flask with a reflux condenser and drying tube and diluted with methylene chloride (5 ml), thionyl chloride (4 ml), and DMF (3 drops). The mixture was heated at reflux for 1 hour and the resulting colorless solution was evaporated to an oil (5). The oil that was diluted with benzene (5 ml), evaporated to dryness in vacuo twice, diluted with methylene chloride (4 ml) and used directly in the preparation of 6.

Example

5-Chloro-2-thiophenecarbonyl chloride (4)

5-Chlorothiophene-2-carboxylic acid (48.8 g, 300 mmol) was placed in a 500 ml round bottom flask with a reflux condenser and drying tube and treated with thionyl chloride (120 ml), and DMF (0.5 ml). The mixture was heated at reflux for 5 hours and the resulting clear yellow solution was evaporated to an oil (5). The oil that was diluted with ethyl acetate (100 ml) (forming a clear solution indicative of complete conversion to the acid chloride), evaporated to dryness in vacuo and diluted with ethyl acetate (100 ml) again and evaporated to an oil. The oil was dissolved in methylene chloride (150 ml) forming a clear yellow solution used directly in the preparation of 5.

Example

5-Chloro-N-({(5S)-2-oxo-3-[4-(3-oxomorpholino-4-yl)phenyl]-1,3-oxazolidine-5-yl}methyl)-thiophene-2-carboxamide (5)

To a 50 ml 3 neck round bottom flask with stirring bar was added water (5 ml), 12 N hydrochloric acid (0.5 ml, 6 mmol), methylene chloride (4 ml) and (S)-(E,Z)-5-((4-chlorobenzylideneamino)methyl)-3-(4-morpholin-3-onephenyl)oxazolidin-2-one (4) (828 mg, 2 mmol). The mixture was rapidly stirred and within 15 minutes a clear two-phase solution resulted. The reaction was stirred an additional 45 minutes and the lower organic layer discarded. The colorless aqueous layer was washed with additional methylene chloride (2×5 ml) and the methylene chloride was discarded. Methylene chloride (5 ml) was added to the aqueous layer and the two phase solution was transferred to a 125 ml Erlenmeyer flask, cooled in an ice bath and basified to ca. pH 9 to 10 with ice cold 6 N NaOH. A solution of 5-chloro-2-thiophenecarbonyl chloride (4) (6 mmol) in methylene chloride (4 ml) was added all at once to the rapidly stirring solution and gas evolution/foaming was observed. The reaction mixture was removed from the ice bath and stirred at room temp for 30 minutes. The resulting reaction mixture containing white crystals was cooled in an ice bath and the crystals (6) were collected on a sintered glass Buchner funnel and washed with ether. The product was dried in a vacuum oven at 40° C. (600 mg, 69%). TLC (CH$_2$Cl$_2$: MeOH 9:1) Rf=0.5). Recrystallization from methanol provided white crystals (400 mg). mp 229-230° C. (Lit$^2$ mp 230° C.). LCMS Retention Time: 4.31 min m/e 436 (M+H)$^+$, 494 (M+59)$^+$. $^1$H NMR (500 MHz, DMSO-d6) δ 8.98 (t, 1H, J=5.8 Hz), 7.69 (d, 1H, J=4.1 Hz), 7.56 (d, 2H, J=9 Hz), 7.40 (d, 2H, J=9.0 Hz), 7.19 (d, 1H, J=4.1 Hz), 4.84 (m, 1H), 4.19 (s, 2H), 4.188 (t, 1H, J=10.6 Hz), 3.97 (dd, 2H, J=4.7 Hz, J=4.7 Hz), 3.84 (dd, 1H, J=9.1 Hz, J=6.2 Hz), 3.71 (t, 2H, J=5.2 Hz). [α]$^{23}_D$ −45.1° (c=1.00, DMSO) (Lit.$^2$ [α]$_D^{21}$ −38° (c=1.00, DMSO). Chiral chromatography: Retention time: 24.19 min (100%)>98% ee) (m/e 436, 494).

Example

5-Chloro-N-({(5S)-2-oxo-3-[4-(3-oxomorpholino-4-yl)phenyl]1,3-oxazolidine-5-yl}methyl)-thiophene-2-carboxamide (rivaroxaban, 5)

To a 3 L-3 neck round bottom flask with overhead stirrer was added water (250 ml), 12 N hydrochloric acid (25 ml, 300 mmol), methylene chloride (150 ml) and (S)-(E,Z)-5-((4-chlorobenzylideneamino)methyl)-3-(4-morpholin-3-onephenyl)oxazolidin-2-one (4) (41 g, 99 mmol) that was washed in with methylene chloride (75 ml). The mixture was rapidly stirred and within 15 minutes a clear light yellow two-phase solution resulted. The reaction was stirred an additional 1 hour 15 minutes and the lower organic layer discarded. The colorless aqueous layer was washed with additional methylene chloride (2×75 ml) and the methylene chloride was discarded. Methylene chloride (225 ml) was added to the aqueous layer and the two phase solution was transferred back to the 3 L-3neck round bottom flask with overhead stirrer. The reaction was cooled in an ice bath and basified to ca. pH 9 to 10 with ice cold 6 N NaOH. The two phase solution was rapidly stirred and a solution of 5-chloro-2-thiophenecarbonyl chloride (4) (300 mmol) in methylene chloride (150 ml) was added all at once to the rapidly stirring solution and gas evolution/foaming was observed. The reaction mixture was removed from the ice bath and stirred at room temp for 30 minutes. A thick white mass of crystalline solid formed within a few minutes. The crystals of 5 were collected by filtration and washed with cold (−15° C.) methanol (100 ml) and then ether. The product was dried in a vacuum oven at 40° C. for 16 hours (40.53 g, 94%). TLC ($CH_2Cl_2$:MeOH 9:1) Rf=0.5). Recrystallization from glacial acetic acid (350 ml) provided shiny white crystals (36.0 g, 83.7%). mp 229-230° C. (Lit[2] mp 230° C.). LCMS (Method 2) Retention time: 15.79 min (100%) m/e 474 (M+K)[+]. $^1$H NMR (500 MHz, DMSO-d6) δ 8.98 (t, 1H, J=5.8 Hz), 7.69 (d, 1H, J=4.1 Hz), 7.55 (d, 2H, J=9 Hz), 7.40 (d, 2H, J=9.0 Hz), 7.19 (d, 1H, J=4.1 Hz), 4.84 (m, 1H), 4.19 (s, 2H), 4.188 (t, 1H, J=10.6 Hz), 3.97 (dd, 2H, J=4.7 Hz, J=4.7 Hz), 3.84 (dd, 1H, J=9.1 Hz, J=6.2 Hz), 3.71 (t, 2H, J=5.1 Hz), 3.60 (t, 2H, J=5.4 Hz). $[\alpha]^{23}_D$ −38.0° (c=1.00, DMSO) (Lit.[2] $[\alpha]^{21}_D$ −38° (c=1.00, DMSO). Chiral chromatography: Retention time: 24.19 min (100%)>98% ee) m/e 436 (MH)+.

Example

S(E,Z)-1-(4-Chlorobenzylideneamino)-3-chloropropan-2-ol (7)

4-Chlorobenzaldehyde (15.7 gm 112 mmol), methanol (50 ml) and conc $NH_4OH$ (10 g, 172 mmol) were added to a 250 ml round bottom flask with football stirring bar. (S)-Epichlorohydrin (6) (10 g, 8.5 ml, 108 mmol) (Atlantic SciTech Group, Inc) (98% purity) was added and the colorless reaction solution was heated at 40° C. (bath temp) for 6 hr with stirring and allowed to stand at room temp overnight. GCMS analysis of the reaction solution indicated complete reaction. The reaction solution was diluted with methylene chloride (100 ml) and brine (75 ml). The organic layer was separated and the aqueous layer extracted with additional methylene chloride (25 ml). The combined organic layer was washed with brine (50 ml), dried (MgSO4) and evaporated to a white crystalline solid. (In previous runs initially isolated as an oil that was seeded). The crystals were treated with hexane (30 ml), cooled overnight at −15° C. and collected by filtration, air dried and then dried in a vacuum oven for 3 hours at room temp (19.5 g, 75%); $^1$H NMR (500 MHz, DMSO-d6) δ 8.34 (s, 1H), 7.78 (d, 2H, J=8.5 Hz)), 7.52 (d, 2H, J=8.5 Hz), 5.29 (d, 1H, J=5.4 Hz), 3.94 (dd, 1H, J=13 Hz, J=6.1 Hz), 3.25 (br ddd, 1H, J=6.5 Hz, J=3.5 Hz, J=2.8 Hz), 2.65 (dd, 1H, J=5 Jz, J=2.6 Hz), 2.77 (dd, 1H, J=5 Hz, J=4.1 Hz); GCMS Retention time 10.03 min (m/e 232)

Example (S) (E,Z)-N-4-Chlorobenzylidene-1-(oxiran-2-yl)methanamine (8)

(S) (E,Z)-1-(4-Chlorobenzylideneamino)-3-chloropropan-2-ol (7) (163 g, 0.7 mol), reagent grade methanol (1.5 L) and anhydrous $K_2CO_3$ (193 g, 1.4 mol) were added to a 3 L 3 neck round bottom flask with overhead stirrer. The reaction mixture was stirred vigorously. After 2 hrs GCMS showed complete conversion to the epoxide (Small aliquot removed from the reaction, diluted with an equal volume of $CH_3CN$, filtered thru disposable pipette with a cotton plug). The colorless reaction was diluted with CH2Cl2 (1 L), brine (800 ml) and water (200 ml). The aqueous layer was extracted with additional CH2Cl2 (250 ml). The combined organic layers were washed with brine (4×200 ml), dried (MgSO4) and evaporated (bath temp 45° C.) to a colorless oil (136 g, quantative); $^1$HNMR (500 MHz, DMSO-d6) δ 8.35 (s, 1H), 7.78 (d, 2H, J=8.2 Hz)), 7.53 (d, 2H, J=8.2 Hz), 3.89 (ddd, 1H, J=13 Hz, J=3.5 Hz, J=1.6 Hz), 3.55 (ddd, 1H, J=13 Hz, J=6.1 Hz, J=1.3 Hz), 3.25 (br ddd, 1H, J=6.5 Hz, J=3.5 Hz, J=2.8 Hz), 2.65 (dd, 1H, J=5 Jz, J=2.6 Hz), 2.77 (dd, 1H, J=5 Hz, J=4.1 Hz); GCMS Retention time 8.98 min (m/e 194).

Example

Recrystallization of 5-Chloro-N-({(5S)-2-oxo-3-[4-(3-oxomorpholino-4-yl)phenyl]-1.3-oxazolidine-5-yl}methyl)-thiophene-2-carboxamide (rivaroxaban, 5) from Propionic acid 5-Chloro-N-({(5S)-2-oxo-3-[4-(3-oxomorpholino-4-yl)phenyl]-1.3-oxazolidine-5-yl}methyl)-thiophene-2-carboxamide (rivaroxaban) (1.0 gm) was dissolved in propionic acid (11 ml) by heating the mixture to reflux with stirring. The colorless solution with was allowed to cool slowly to room temperature with stirring. White crystals started to form while the solution was still warm. The crystalline mixture was cooled to room temperature with stirring. The white crystals were collected by filtration, washed with propionic acid (1 ml) and cold methanol (3 ml). The crystals were dried under high vacuum at 100° C. for 16 hours (940 mg) mp 229-230° C. LCMS Retention time: 14.10 min (100%) m/e 446 (M=H), 474 (M+K)[+]. $^1$H NMR (500 MHz, DMSO-d6) δ 8.98 (t, 1H, J=5.8 Hz), 7.69 (d, 1H, J=4.1 Hz), 7.55 (d, 2H, J=9 Hz), 7.40 (d, 2H, J=9.0 Hz), 7.19 (d, 1H, J=4.1 Hz), 4.84 (m, 1H), 4.19 (s, 2H), 4.188 (t, 1H, J=10.6 Hz), 3.97 (dd, 2H, J=4.7 Hz, J=4.7 Hz), 3.84 (dd, 1H, J=9.1 Hz, J=6.2 Hz), 3.71 (t, 2H, J=5.1 Hz), 3.60 (t, 2H, J=5.4 Hz). LCMS was performed under the following condition:

Column: Inertsil Ph, 5 micron, 250×4.6 mm; Solvent A: 1.36 g $KH_2PO_4$ in 1000 mL $H_2O$, adjust to pH 7.0 with 1N KOH; Solvent B: $CH_3CN$; Method: Time 0 min 70% B, Time 8 min 70% B, Time 15 min 50% B, Time 30 min 30% B, Time 40 min 30% B, Stop time: 40 min, Gradient elution flow rate 1.00 ml/min Additional optional synthetic details are described in Mederski et al. *Heterocycles* 2007, 74, 437-445, and Roehrig et al. *J. Med. Chem.* 2005, 49, 5900-5908, the disclosures of which are incorporated herein by reference. It is to be understood that the foregoing illustrative examples may be modified with the appropriate selection of starting materials to prepare other compounds described herein.

Example (S)(E,Z)-1-(Benzylideneamino)-3-chloropropan-2-ol (12)

Benzaldehyde (5.95 g, 56 mmol), ethanol (25 ml) and conc. $NH_4OH$ (5 g, 85 mmol) were added to a 100 ml round bottom flask with football stirring bar (resulting in a mild exotherm). (S)-Epichlorohydrin (5 g, 4.25 ml, 54 mmol) was added and the colorless reaction solution was heated at 40° C. (bath temperature) for 6 hr with stirring and allowed to stand at room temperature overnight. The reaction solution was evaporated to a colorless thick oil and diluted with water (5 ml). The solution was cooled on Dry Ice and then allowed to warm to room temperature forming white crystals (seeding—but not necessary). Decanted the water from the fine crystals (difficult to filter) and removed the rest of the water by warming the round bottom containing the crystals at 40° C. under high vacuum. (Crystals partially melted during the 30 min—cooled in an ice bath while continuing to pull vacuum at the end of the 30 min). The white crystals were recrystallized from 300 ml of hot hexane removing a small amount of insoluble material by treating with Celite followed by gravity filtration through fluted filter paper—concentrated via reflux to 100 ml, cooled to room temperature and then in an ice bath. The resulting white crystals were collected by filtration and dried at room temperature (House vacuum) (7.53 g, 70.6%), GCMS retention time 8.84 min, m/e 196.

Example (S)(E,Z)-N-benzylidene-1-(oxiran-2-yl)methanamine (10)

(S)(E,Z)-1-(Benzylideneamino)-3-chloropropan-2-ol (12) (2.55 g, 12.9 mmol), reagent grade methanol (65 ml) and anhydrous $K_2CO_3$ (3.56 g, 25.8 mmol) were added to a 250 ml round bottom flask with football stirrer and drying tube. The reaction mixture was stirred vigorously (rate of stirring determines rate of heterogenous reaction). After 2 hrs GCMS showed complete conversion to the epoxide (small aliquot removed from the reaction, diluted with an equal volume of $CH_3CN$, filtered through pipette with a cotton plug in a disposable pipette). Retention time 7.77 min, m/e 160 (the methoxyalcohol from opening the epoxide has retention time 8.67 min m/e 192) (substantial formation of this material observed if reaction allowed to proceed overnight). The coloreless reaction was diluted with $CH_2Cl_2$ (100 ml) and the aqueous layer was extracted with additional $CH_2Cl_2$ (2×50 ml). The combined organic layers were washed with brine (3×100 ml), dried ($MgSO_4/Na_2SO_4$) and evaporated to a colorless oil (2.1 g, quantitative yield); $^1$H NMR (500 MHz, $CDCl_3$) δ 8.29 (s, 1H), 7.73-7.75 (m, 2H), 7.40-7.43 (m, 3H), 3.90-3.93 (m, 1H), 3.68-3.72 (m, 1H), 3.32-3.35 (m, 1H), 2.84-2.87 (m, 1H), 2.73-2.75 (m, 1H); MS (EI, 70 eV) m/z 161 ($M^+$, 3), 160 (17), 144 (23), 132 (39), 118 (43), 104 (53), 91 (100). GCMS shows essentially pure epoxide; used directly to prepare 11. GCMS Retention time 7.76 min (m/e 160).

Example (S)(E,Z)-1-(4-Chlorobenzylideneamino)-3-chloropropan-2-ol (7)

4-Chlorobenzaldehyde (7.85 g, 56 mmol), ethanol (25 ml) and conc $NH_4OH$ (5 g, 86 mmol) were added to a 100 ml rd bottom flask with football stirring bar. (S)-Epichlorohydrin (5 g, 4.25 ml, 54 mmol) (TCI America, Lot: AZR7B, min 98% purity) was added and the colorless reaction solution was heated at 40° C. (bath temp) for 6 hr with stirring and allowed to stand at room temp overnight. The reaction solution was diluted with methylene chloride (150 ml) and brine (125 ml). The organic layer was separated and the aqueous layer extracted with additional methylene chloride (50 ml). The combined organic layers were washed with brine (75 ml), dried ($MgSO_4$) and evaporated to dryness yielding a colorless oil that was crystallized from hexane (9.0 g, 72%). GCMS Retention time 10.03 min (m/e 232).

Example (S)(E,Z)-1-(4-Chlorobenzylideneamino)-3-chloropropan-2-ol (7)

Alternative procedure. 4-Chlorobenzaldehyde (15.7 gm 112 mmol), methanol (50 ml) and conc $NH_4OH$ (10 g, 172 mmol) were added to a 250 ml round bottom flask with football stirring bar. (S)-Epichlorohydrin (10 g, 8.5 ml, 108 mmol) (Atlantic SciTech Group, Inc) (98% purity) was added and the colorless reaction solution was heated at 40° C. (bath temp) for 6 hr with stirring and allowed to stand at room temp overnight. GCMS analysis of the reaction solution indicated complete reaction. The reaction solution was diluted with methylene chloride (100 ml) and brine (75 ml). The organic layer was separated and the aqueous layer extracted with additional methylene chloride (25 ml). The combined organic layer was washed with brine (50 ml), dried ($MgSO_4$) and evaporated to a white crystalline solid. (In previous runs initially isolated as an oil that was seeded). The crystals were treated with hexane (30 ml), cooled overnight at −15° C. and collected by filtration, air dried and then dried in a vacuum oven for 3 hours at room temp (19.5 g, 75%); $^1$H NMR (500 MHz, DMSO-$d_6$) δ 8.34 (s, 1H), 7.78 (d, 2H, J=8.5 Hz)), 7.52 (d, 2H, J=8.5 Hz), 5.29 (d, 1H, J=5.4 Hz), 3.94 (dd, 1H, J=13 Hz, J=6.1 Hz), 3.25 (br ddd, 1H, J=6.5 Hz, J=3.5 Hz, J=2.8 Hz), 2.65 (dd, 1H, J=5 Jz, J=2.6 Hz), 2.77 (dd, 1H, J=5 Hz, J=4.1 Hz); GCMS Retention time 10.03 min (m/e 232).

Example

Scale-up of the synthesis of (S)(E,Z)-1-(4-chlorobenzylideneamino)-3-chloropropan-2-ol (7)

4-Chlorobenzaldehyde (157 g 1.12 mol), ethanol (500 ml) and conc $NH_4OH$ (100 g, 1.72 mol) were added to a 2 L round bottom flask with football stirring bar. (S)-Epichlorohydrin (100 g, 85 ml, 1.08 mol) (Atlantic SciTech Group, Inc) (98% purity) was added and the colorless reaction solution was heated at 40° C. (bath temp) for 6 hr with stirring and allowed to stand at room temp overnight. GCMS analysis of the reaction solution indicated complete reaction. The reaction solution was diluted with methylene chloride (1 L) and brine (700 ml). The organic layer was separated and the aqueous layer extracted with additional methylene chloride (250 ml). The combined organic layer was washed with brine (500 ml), dried ($MgSO_4$) and evaporated to a white crystalline solid. (Note: In previous smaller runs initially isolated as an oil that was seeded). The crystals were treated with hexane (200 ml), cooled in an ice bath and collected by filtration and washed with 50 ml of cold (−20° C.) hexane, air dried and then dried in a vacuum oven for 3 hours at room temp (165 g, 66%); $^1$H NMR (500 MHz, DMSO-$d_6$) δ 8.34 (s, 1H), 7.78 (d, 2H, J=8.5 Hz), 7.52 (d, 2H, J=8.5 Hz), 5.29 (d, 1H, J=5.4 Hz), 3.94 (dd, 1H, J=13 Hz, J=6.1 Hz), 3.25 (br ddd, 1H, J=6.5 Hz, J=3.5 Hz, J=2.8 Hz), 2.65 (dd, 1H, J=5 Jz, J=2.6 Hz), 2.77 (dd, 1H, J=5 Hz, J=4.1 Hz); GCMS Retention time 10.03 min (m/e 232).

Example (S) (E,Z)-N-4-Chlorobenzylidene-1-(oxiran-2-yl)methanamine (16). (S) (E,Z)-1-(4-Chlorobenzylideneamino)-3-chloropropan-2-ol (7)

(8.9 g, 38.4 mmol), reagent grade methanol (250 ml) and anhydrous $K_2CO_3$ (10.5 g, 76.7 mmol) were added to a 500 ml rd bottom flask with football stirrer. The reaction mixture was stirred vigorously. After 2 hrs GCMS showed complete conversion to the epoxide (Small aliquot removed from the reaction, diluted with an equal volume of $CH_3CN$, filtered thru disposable pipette with a cotton plug) Retention time 8.95 min, m/e 194. The colorless reaction was diluted with $CH_2Cl_2$ (150 ml) and brine (100 ml). The aqueous layer was extracted with additional $CH_2Cl_2$ (75 ml). The combined organic layers were washed with brine (3×75 ml), dried ($MgSO_4$) and evaporated (bath temp 45° C.) to a colorless oil (6.9 g, 92%); $^1H$ NMR (500 MHz, DMSO-$d_6$) δ 8.35 (s, 1H), 7.78 (d, 2H, J=8.2 Hz)), 7.53 (d, 2H, J=8.2 Hz), 3.89 (ddd, 1H, J=13 Hz, J=3.5 Hz, J=1.6 Hz), 3.55 (ddd, 1H, J=13 Hz, J=6.1 Hz, J=1.3 Hz), 3.25 (br ddd, 1H, J=6.5 Hz, J=3.5 Hz, J=2.8 Hz), 2.65 (dd, 1H, J=5 Jz, J=2.6 Hz), 2.77 (dd, 1H, J=5 Hz, J=4.1 Hz); GCMS Retention time 8.95 min (m/e 194).

Example

Scale-up of synthesis of (S) (E,Z)-N-4-chlorobenzylidene-1-(oxiran-2-yl)methanamine (16). (S) (E,Z)-1-(4-Chlorobenzylideneamino)-3-chloropropan-2-ol (7)

(163 g, 0.7 mol), reagent grade methanol (1.5 L) and anhydrous $K_2CO_3$ (193 g, 1.4 mol) were added to a 3 L 3 neck round bottom flask with overhead stirrer. The reaction mixture was stirred vigorously. After 2 hrs GCMS showed complete conversion to the epoxide (small aliquot removed from the reaction, diluted with an equal volume of $CH_3CN$, filtered through disposable pipette with a cotton plug). The colorless reaction was diluted with $CH_2Cl_2$ (1 L), brine (800 ml) and water (200 ml). The aqueous layer was extracted with additional $CH_2Cl_2$ (250 ml). The combined organic layers were washed with brine (4×200 ml), dried ($MgSO_4$) and evaporated (bath temp 45° C.) to a colorless oil (136 g, quantitative); $^1H$ NMR (500 MHz, DMSO-$d_6$) δ 8.35 (s, 1H), 7.78 (d, 2H, J=8.2 Hz)), 7.53 (d, 2H, J=8.2 Hz), 3.89 (ddd, 1H, J=13 Hz, J=3.5 Hz, J=1.6 Hz), 3.55 (ddd, 1H, J=13 Hz, J=6.1 Hz, J=1.3 Hz), 3.25 (br ddd, 1H, J=6.5 Hz, J=3.5 Hz, J=2.8 Hz), 2.65 (dd, 1H, J=5 Jz, J=2.6 Hz), 2.77 (dd, 1H, J=5 Hz, J=4.1 Hz); GCMS Retention time 8.98 min (m/e 194).

What is claimed is:

1. A process for preparing rivaroxaban or a pharmaceutically acceptable salt thereof, the process comprising
   (a) mixing a compound of formula (A)

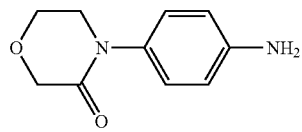

(A)

or a salt thereof, with an acylating agent to prepare a compound of formula (B)

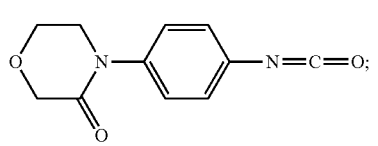

(B)

(b) crystallizing the compound of formula (B);
(c) mixing the compound of formula (B) with a compound of formula (C)

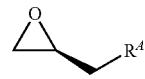

(C)

to prepare a compound of formula (D)

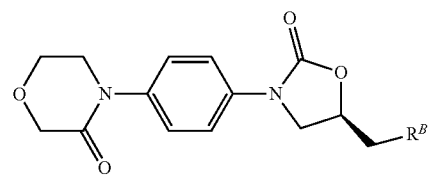

(D)

or a salt thereof; where $R^A$ is halo or a protected amino group; and $R^B$ is halo, amino or a salt thereof, or a protected amino group; and
(d) crystallizing the compound of formula (D);
and, the process further comprising one or more steps selected from the group consisting of
(e) converting the compound of formula (D) or a salt thereof, where $R^B$ is halo, or a protected amino group, into a compound of formula (E)

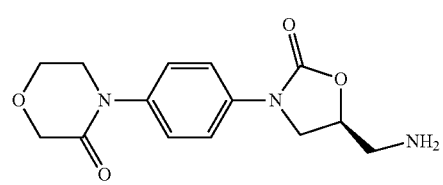

(E)

or a salt thereof;
(f) converting the compound of formula (D) or a salt thereof, where $R^B$ is halo, into a compound of formula (F)

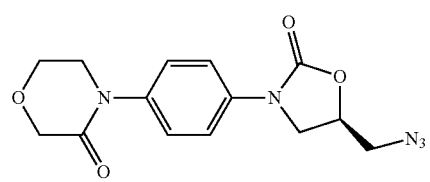

(F)

by contacting the compound of formula (D) with sodium azide;
(g) reducing the compound of formula (F), or a salt thereof, into a compound of formula (E), by contacting the compound of formula (F) with a reducing agent;
(h) mixing the compound of formula (E), or a salt thereof, with an acylating agent to prepare rivaroxaban, or a salt thereof; and
(i) crystallizing rivaroxaban or a salt thereof from an organic acid;
and combinations thereof, wherein step (c) includes a halide catalyst and the halide catalyst is magnesium bromide etherate, lithium bromide, or lithium bromide in combination with a phosphine oxide, such as tri-n-butylphosphine oxide.

2. The process of claim 1 wherein the organic acid is an alkyl carboxylic acid.

3. The process of claim 1 wherein the organic acid is acetic acid.

4. The process of claim 1 wherein the organic acid is propionic acid.

5. The process of claim 1 wherein the acylating agent in step (a) is phosgene or a phosgene analog.

6. The process of claim 1 comprising step (e).

7. The process of claim 1 comprising step (f).

8. The process claim 1 wherein the compound of formula (C) is a compound of the formula

9. The process of claim 1 wherein the compound of formula (C) is a compound of the formula

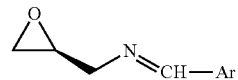

where Ar is optionally substituted phenyl.

10. The process of claim 9 wherein Ar is phenyl.

11. The process of claim 9 wherein Ar is 4-chlorophenyl.

12. The process of claim 1 wherein $R^B$ is an imine.

13. The process of claim 1 wherein $R^B$ is optionally substituted benzylidene amino.

14. The process of claim 1 wherein $R^B$ is benzylidene amino, 4-chlorobenzylidene amino; 4-bromobenzylidene amino; or 2,4-dichlorobenzylidene amino.

15. The process of claim 1 wherein $R^B$ is benzylidene amino.

16. The process of claim 1, wherein the reducing agent in step (g) is hydrogen gas.

17. The process of claim 16, wherein step (g) includes a metal or metal catalyst.

18. The process of claim 1, wherein the halide catalyst is lithium bromide.

* * * * *